United States Patent [19]

Karson et al.

[11] Patent Number: 5,527,825
[45] Date of Patent: Jun. 18, 1996

[54] METHOD OF TREATING SCHIZOPHRENIA, TOURETTE'S SYNDROME, MANIA, AUTISM, AND OBSESSIVE COMPULSIVE DISORDER WITH INHIBITORS OF BRAIN NITRIC OXIDE SYNTHASE

[75] Inventors: Craig N. Karson; Melvin Lyon; Bobby L. Freeman, all of Little Rock, Ark.

[73] Assignee: University of Arkansas, Little Rock, Ark.

[21] Appl. No.: 223,776

[22] Filed: Apr. 6, 1994

[51] Int. Cl.$^6$ .......................... A61K 31/22; A61K 31/195
[52] U.S. Cl. ............................ 514/551; 514/564; 514/565
[58] Field of Search ................................. 514/564, 565, 514/551

[56] References Cited

U.S. PATENT DOCUMENTS 5,266,594  11/1993  Dawson et al. ........................ 514/560

OTHER PUBLICATIONS

Maiese et al., *Chemical Abstracts*, vol. 119, No. 19, abstract 196530r, 1993.
Fujisawa et al., *Chemical Abstracts*, vol. 120, No. 9, abstract 95464n, 1993.
Flavin et al., *Chemical Abstracts*, vol. 120, No. 11, abstract 131320y, 1993.
Riederer et al, *Journal of Neural Transmission*, vol. 34, 1991, pp. 230–210.
Karson et. al., *Psychiatry Research: Neuro imaging*, 40:31–48 (1991).

*Primary Examiner*—Raymond Henley, III
*Assistant Examiner*—William R. A. Jarvis
*Attorney, Agent, or Firm*—Benjamin Aaron Adler

[57] ABSTRACT

The present invention provides a pharmaceutical compositions suitable for the treatment of brain diseases characterized by excessive activity of brain dopamine systems and/or nitric oxide systems. Also provided is a method of treating psychiatric and neurologic diseases.

9 Claims, 3 Drawing Sheets

METHOD OF TREATING SCHIZOPHRENIA, TOURETTE'S SYNDROME, MANIA, AUTISM, AND OBSESSIVE COMPULSIVE DISORDER WITH INHIBITORS OF BRAIN NITRIC OXIDE SYNTHASE

BACKGROUND OF THE INVENTION

1. Field of the Invention

The present invention relates generally to the fields of biological psychiatry and neuropharmacology. More specifically, the present invention relates to a novel method of treating dysfunctional dopaminergic and nitric oxide related activity and related psychiatric and neurologic diseases.

2. Description of the Related Art

A wide variety of psychiatric and neurologic pathophysiologic states are believed to involve dysfunction of brain neurotransmitter and neuropeptide systems. A monoaminergic neurotransmitter that has drawn considerable attention over the last generation is dopamine. Anti-dopaminergic drugs, such as the neuroleptics haloperidol and chlorpromazine, have been the drugs of choice for various psychiatric and neurologic diseases such as schizophrenia. Despite moderate success, the antipsychotic dopamine antagonists have serious medical drawbacks including the gradual induction of permanent dyskinesias and a failure to counteract abnormal cholinergic interactions with dopamine. Thus, safer and more efficacious means of treating diseases such as schizophrenia are highly desirable.

A salient animal model has recently been developed for certain aspects of schizophrenic behavior and brain pathology. This animal model involves prenatal exposure to d-amphetamine in the rat in which there are early juvenile signs of behavioral changes suggestive of hypodopaminergia, followed by an increasing sensitivity to ultradian rhythm changes in striatal dopamine activity. As the offspring approach adulthood, there are significant increases in bodily activity, suggesting increased dopamine activity in the post-pubertal period. There are also gradual increases in switching between alternative response possibilities, poorer reversal learning and finally increased perseveration in simple response, all of which have been characterized not only as functions of dopamine overstimulation in animals and humans but also as significant symptoms in schizophrenic patients.

In parallel, this animal model also shows changes in neuronal number in three brain regions similar to reported changes found in schizophrenia. Neuronal losses in the mediodorsal thalamic nucleus and in the nucleus accumbens both in schizophrenia and in animals exposed to prenatal d-amphetamine have been described. In contrast, there are increased numbers of nitric oxide synthetase (NOS)-containing cholinergic neurons in the pedunculopontine and laterodorsal tegmental nuclei (PPTg/LDTg) in this animal model just as there are in schizophrenia. These cholinergic neurons can release nitric oxide and also directly affect the dopaminergic activity in the brain via the nigrostriatal pathway The prior art is deficient in the lack of effective means of treating dopamine and nitric oxide dysfunctional states, in disorders such as schizophrenia in a manner that include treatment of the effect produced by these cholinergic, nitric oxide synthetase containing neurons. The present invention fulfills this need and desire in the art.

SUMMARY OF THE INVENTION

In one embodiment of the present invention, there is provided a pharmaceutical composition suitable for the treatment of brain diseases, said pharmaceutical composition comprising an inhibitor of brain nitric oxide synthetase and a pharmaceutically acceptable carrier.

In another embodiment of the present invention, there is provided a method of treating brain diseases characterized by excess activity of a brain dopaminergic system, comprising the step of administering an inhibitor of brain nitric oxide synthetase to an individual having said disease.

In yet another embodiment of the present invention, there is provided a method of pharmacologically treating schizophrenia, comprising the step of administering an inhibitor of brain nitric oxide synthetase to an individual in need of treatment.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope. These drawings illustrate the utility of the present invention using the fetal development animal model of schizophrenia.

DETAILED DESCRIPTION OF THE INVENTION

The present invention is directed to a pharmaceutical composition suitable for the treatment of brain diseases characterized by excess activity of a dopaminergic system, comprising an inhibitor of nitric oxide synthetase and a pharmaceutically acceptable carrier.

Generally, any inhibitor of brain nitric oxide synthetase will be useful in the pharmaceutical composition and methods of the present invention. Representative examples of inhibitors of brain nitric oxide synthetase include nitro-L-arginine, N-imino ethyl-L-ornithine, L-canavanine and N-monomethyl-L-arginine. Preferably, the inhibitor of brain nitric oxide synthetase is nitro-L-arginine or a methyl ester thereof. A person having ordinary skill in this art would readily recognize that the art contains various methods of effectively reducing brain nitric oxide levels. Given the teachings of the present invention, a person having ordinary skill in this art would readily appreciate the advantages of using a drug, other than a nitric oxide synthesis inhibitor, which effectively antagonizes or inhibits the biological/neurochemical effects of nitric oxide for the purpose of treating certain brain diseases such as schizophrenia.

Generally, the pharmaceutical compositions and methods of the present invention will be useful in treating psychiatric and neurologic diseases characterized by an excessive activity in brain dopaminergic and nitric oxide systems. Thus, the pharmaceutical compositions and methods of the present invention will be useful in treating such diseases such as schizophrenia, mania, Gilles de la Tourette's Syndrome, Alzheimer's Disease, autism and obsessive compulsive disorder. Generally, the pharmaceutical compositions and methods of the present invention will be most useful in treating diseases currently treated with either "typical" or "atypical" neuroleptics, i.e. haloperidol, clozapine, etc.

The present invention also provides a method of treating brain diseases characterized by excess activity of a dopaminergic system, comprising the step of administering an inhibitor of nitric oxide synthetase to an individual having said disease. Furthermore, the present invention also contains as one embodiment, a method of pharmacologically treating schizophrenia, comprising the step of administering an inhibitor of brain nitric oxide synthetase to an individual in need of treatment.

It is specifically contemplated that pharmaceutical compositions are prepared in the present invention. A person having ordinary skill in this art would readily be able to determine, without undue experimentation, the appropriate dosages and routes of administration in the present invention. The pharmaceutical compositions of the present invention are suitable for use in a variety of drug delivery systems. For a brief review of present methods for drug delivery, see Langer, Science, 249:1527–1533 (1990). Methods for preparing administrable compounds will be known or apparent to those skilled in the art and are described in more detail, for example, in Remington's Pharmaceutical Science, 17th ed., Mack Publishing Company, Easton, Pa. (1988). Generally, the dose at which the inhibitor of brain nitric oxide is given is any that effectively reduces the synthesis of brain nitric oxide. A person having ordinary skill in this art would readily be able to determine the optimal dose of an inhibitor of brain nitric oxide synthetase. For example, the dose of the brain nitric oxide synthetase inhibitor, nitro-L-arginine, would be contained in the pharmaceutical composition would be in an amount of from about 1 milligrams/kg to about 30 milligrams/kg.

Animal Model of Schizophrenia

The animal model used in the following illustrative example is based on testing the offspring of pregnant female rats treated with d-amphetamine during mid-pregnancy. The value of a fetal growth model for schizophrenia using animals derived from the obvious difficulties of relying solely upon data from the excellent, but extremely long-term, developmental investigations of children with a genetically high risk for schizophrenia. Such studies require 20 to 30 years of human development, whereas in the rat this same growth period may be investigated in as little as two years. Among the advantages of choosing the rat for animal model of schizophrenia are the following: (1) control of subjects genetically and behaviorally; (2) ability to follow lifetime developments in a period of two–three years; (3) small physical size and economy of maintenance; and (4) many physiological similarities to humans, including basic brain structure, neurotransmitters, and response to pharmacological agents.

In the rat, the developmental phase in the brain parallel to that of the human second trimester begins approximately at the 12th gestational day fifth postnatal day. The postnatal period overlaps with some of the human third trimester brain development, which occurs almost completely after birth in the rat. The period of the 11–14th (or 12–15th) gestational day coincides with the birth and earliest development of cells in subcortical regions of particular importance in schizophrenia, such as the corpus striatum, thalamus and hippocampal formation. The newly born cells then migrate toward their final location, with regions appearing later in phylogeny also being among the last to complete their functional connections. Some neurotransmitters of importance in schizophrenia, such as dopamine and norepinephrine, are already present in cells between the 12–15th days, but the receptors and functional synaptic structure are not completed until after birth. Acetylcholine, and several other neurotransmitters, appear even later and their systems are also not completely functional until after birth.

The present invention illustrates significant behavioral changes related to increased sensitivity to dopaminergic, cholinergic, and nitric oxide stimulation for the amphetamine treatment condition as compared to control conditions. Although there are differences in the time of appearance, the behavioral abnormalities do not seem to be gender specific, since both sexes exhibit the same trends with respect to control animals.

Relationship to Dopaminergic Systems:

Rats fetally exposed to d-amphetamine are more sensitive to dopaminergic stimulation, e.g., by apomorphine. This finding is parallel to the heightened sensitivity to dopaminergic stimulation seen in schizophrenic patients. Furthermore, animals exposed fetally only to undernutrition which may accompany the d-amphetamine treatment were least sensitive to the dopamine challenge, making it unlikely that fetal undernutrition alone might be the causal factor.

Relationship to Cholinergic Systems:

Excessive numbers of nitric oxide synthetase-containing cholinergic cells have been demonstrated in the brainstem PPTg and LDTg nuclei in both human schizophrenics and in rats fetally exposed to d-amphetamine. Amphetamine treated animals were also more sensitive to cholinergic stimulation, as induced by the cholinesterase inhibitor physostigmine. Since physostigmine tends to have an inhibitory effect on nicotinic receptors, the excitatory effects were mainly due to muscarinic receptor action. The fact that rearing was reduced in amphetamine treated animals under physostigmine, while teeth-chattering, a specifically cholinergic response, was significantly increased, also suggests that these effects are not simply due to an indirect dopamine system stimulation. As mentioned above, the undernourished control animals were not especially sensitive to dopaminergic challenge, but at the highest physostigmine dose, did show increased teeth chattering compared to the controls. It appeared that the effect of prenatal undernutrition was more cholinergic than dopaminergic.

Relationship to Nitric Oxide Systems:

An excess number of NOS-containing cholinergic cells in the PPTg and LDTg brainstem nuclei has been found in postmortem schizophrenic brain tissue. The present invention shows that with nitroglycerin, in amphetamine treated animals only, the additional release of nitric oxide directly, or indirectly via changes in blood supply to the brain, causes increased behavioral activity.

The fact that grooming, walking, and rearing were higher in amphetamine treated animals under nitroglycerin appears to indicate an increased dopaminergic stimulation compared to control animals. However, the fact that the complex behavior grooming is increased suggests that the dopaminergic stimulation was not as great with nitroglycerin as it was with apomorphine where licking stereotypy, a sign of advanced dopaminerigic stimulation, appeared.

The effect of the nitric oxide release on rearing is especially noteworthy since rearing, in amphetamine treated animals compared with controls, was increased under nitroglycerin treatment, reduced under physostigmine, and unaffected by apomorphine. It is not likely that this difference was due to the selection of dose levels illustrated in FIG. 1, since for each drug the reported dose is an intermediate one and no evidence for such a suggestion was found at the other dose levels.

The greater amount of head-raising under the d-amphetamine+$N^G$-nitro-L-arginine methyl ester condition showed that amphetamine treated animals could be more active in certain response categories than control animals even when nitric oxide release was almost totally inhibited. The increased head-raising, occurring only in the amphetamine treated animals, is not likely due to the dopaminergic stimulation effect of the d-amphetamine, since amphetamine treated animals showed less walking than the control animals, and head-raising has been associated with stimulation of muscarinic cholinergic receptors. Thus, when nitric oxide activity was reduced to a minimum, the only activity remaining stimulated in the amphetamine treated animals appears to be of a cholinergic nature (HEAD↑). Even though nitric oxide synthase is contained in most brainstem cholinergic neurons, the inhibition of nitric oxide synthetase activity does not prevent the activity of at least some of these cells. In any case, only amphetamine treated animals showed significant behavioral differences under both stimulation and inhibition of nitric oxide activity in the brain.

Animals fetally exposed to d-amphetamine were more sensitive than control animals, that had been exposed to either saline injection or undernutrition, to dopaminergic and cholinergic stimulation. The amphetamine treated animals also showed more activity upon nitric oxide release than control animals. Since the nitric oxide release also caused an increase in rearing, rather than a decrease as under physostigmine, some effects of nitric oxide in animals with prenatal exposure to d-amphetamine may be more closely related to dopaminergic rather than cholinergic stimulation. On the other hand, when nitric oxide activity was strongly inhibited by $N^G$-nitro-L-arginine methyl ester, the amphetamine treated animals showed less locomotion but significantly greater head-up activity, which has been associated with cholinergic stimulation.

The present invention is consistent with the reported hypersensitivity of schizophrenic patients to both dopaminergic and cholinergic stimulation, and with the finding of extra cells in the PPTg and LDTg nuclei in postmortem brain tissue from schizophrenic patients. The present invention also illustrates the importance of controlling the release of nitric oxide in the treatment of schizophrenia.

The following examples are given for the purpose of illustrating various embodiments of the invention and are not meant to limit the present invention in any fashion.

EXAMPLE 1

Method Used to Illustrate the Invention

Subjects

Thirty pregnant Sprague-Dawley females with known sperm plug date, recorded as gestational day 1 (GD 1) were obtained from the National Center for Toxicological Research breeding colony in Jefferson, Ark., to produce offspring. An equal number of dams were used as surrogate mothers for all offspring, which were culled to N=8 and fostered on postnatal day 2. The experimental dams received one of the following three treatments on GD 12–15: (1) saline control injections, s.c.; (2) 5.0 mg/kg d-amphetamine injections, s.c.; (3) an undernutritional diet as control for the anorectic effect of d-amphetamine by feeding them the average amount of food eaten by amphetamine-treated mothers on each day of injection treatment. Except as noted below, one male and one female from each litter were selected for the following experiments.

Behavioral Observations

Subjects were scored, blind to treatment condition, in groups of four animals using cages constructed of wire net, with response sampling procedures. Observations were made in 15 second time samples taken once per minute for a 20 minute session, using the method developed by Fray et al., *Psychopharmacol.* 69:253–259 (1980) for testing behavioral effects of dopaminergic stimulants such as amphetamine and apomorphine.

Using this method, the response categories rated were: stillness, yawning, rearing, sniffing, licking, gnawing, grooming, walking, teeth chattering or gnashing, and head positions mainly up, down, or horizontal. Yawning and sniffing data are not reported here because these signs occurred too seldom or too frequently, respectively, to be statistically useful.

Response categories were rated as present or absent during each 15 second observation period, except during the $N^G$-nitro-L-arginine methyl ester treatment (see below) when all responses were rated as: 0=not present; 1=single instances, definitely discontinuous; 2=many instances, essentially continuous.

Data Analysis

Data were analyzed using Statistical Analysis Systems software (SAS/STAT User's Guide, 1990). In the apomorphine/physostigmine studies, only differences that were significant with a t-test for litter means are reported, in order to minimize effects due to smaller intralitter variance. Since the remaining studies did not have enough litters to meet this statistical criterion, comparisons between treatments were initially examined using the General Linear Models (GLM) procedure in SAS together with the Ryan-Einot-Gabriel-Welsch Multiple Range Test (REGWQ) (SAS/STAT User's Guide, 1990) to control for Type 1 error rate. Only when the results of the GLM test revealed significant differences, were these further explored by the Wilcoxon Rank Sum method after using an F-test to assure for a reasonable homogeneity of variance. Where it was possible to predict the direction of anticipated behavioral change, one-tailed probability values have been reported.

EXAMPLE 2

Apomorphine/Physostigmine Challenge

Apomorphine was chosen as a behaviorally well-characterized dopaminergic (DA) agonist, with isotonic saline for control injections. The apomorphine doses chosen were 0.5 and 1.0 mg/kg because these doses are at the lower limit of doses that produce full-blown stereotypy and at the upper limit of doses that produce yawning. If the offspring were in a hyperdopaminergic state there would be an increased tendency toward repetitive activity and stereotypy, while if the effect were hypodopaminergic, there would be more stillness and yawning. Yawning produced by apomorphine tends to have a specific behavioral form with head level, mouth wide open, but little tongue protrusion. The interaction between brainstem cholinergic systems in the PPTg region and the nigrostriatal dopamine system might be expected to change the level of dopamine activity.

Physostigmine was selected for its acetylcholinesterase inhibiting property which heightens cholinergic (ACh) activity. Isotonic saline was used for control injections. The physostigmine doses chosen were 0.1 and 0.6 mg/kg. The higher dose is at the edge of the dose level producing teeth gnashing or chattering, which is the type of "stereotypy" seen with hypercholinergia. The lower dose usually produces a significant, but less than maximal, number of yawns that are different in form from that seen with apomorphine. In physostigmine-induced yawning the head is stretched upward with tongue protruding. Since the yawning and head-up movements are related to increased cholinergic receptor activity, the larger number of cholinergic cells in the brain stem PPTg/LDTg of the amphetamine rats might be expected to increase the frequency of yawning or head-stretching.

Apomorphine/Physostigmine Challenge

The 16 amphetamine treated animals, the 12 control animals and the 12 undernourished animals used in the apomorphine/physostigmine experiments had been subjected earlier (at postnatal days 24–54) to six trials in a holeboard apparatus with food reinforcement. These animals had reached a fully adult stage of development (i.e. >postnatal day 90). Apomorphine was used first in a counterbalanced series of drug and control (saline) doses given on alternate days and with a one-week pause before a similar counterbalanced series with the physostigmine dose levels.

Apomorphine vs. Physostigmine

Figure 1:
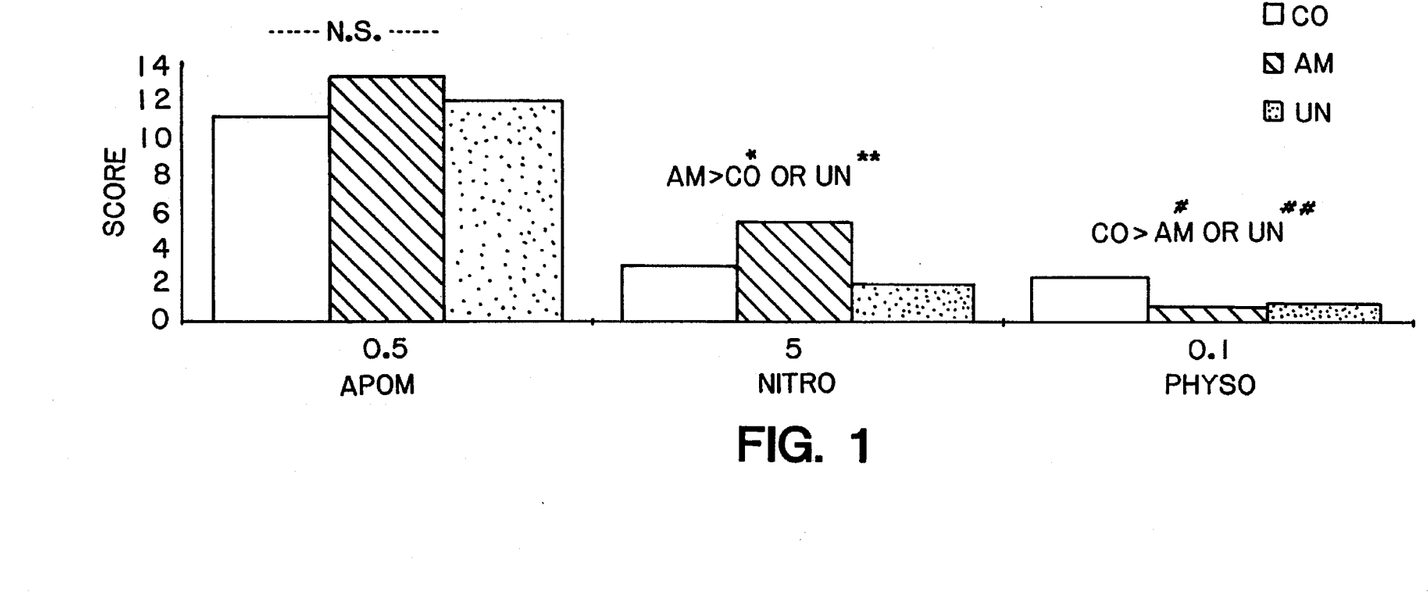
FIG. 1 illustrates the increased sensitivity to nitric oxide releasing compounds in the animal model by showing the rearing behavior in male amphetamine treated, saline control and undernourished animals under 0.5 mg/kg APOMorphine, 5.0 mg/kg NITROglycerin, or 0.1 mg/kg PHYSOstigmine. N.S.=not significant. *[t=2.00, df=16, p=0.03, one-tailed] **[t=2.62, df=14, p=0.02, two-tailed] #[t=2.22, df-11, p=0.05, two-tailed] ##[t=1.99, df=8, p=0.04, one-tailed]
Figure 2A:
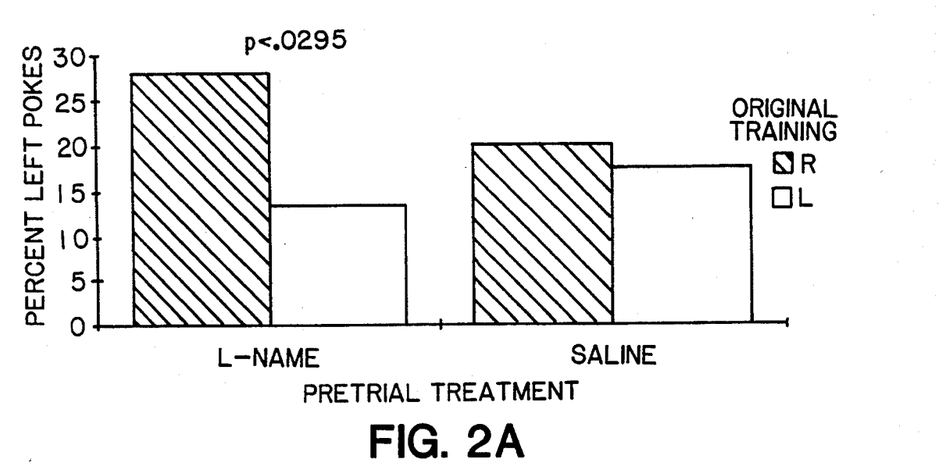
FIG. 2 shows the improved holeboard reversal learning of amphetamine treated animals with the nitric oxide synthetase inhibitor, $N^G$-nitro-L-arginine methyl ester. All animals received prenatal d-amphetamine exposure. p-values from two-tailed t-tests.
Figure 2B:
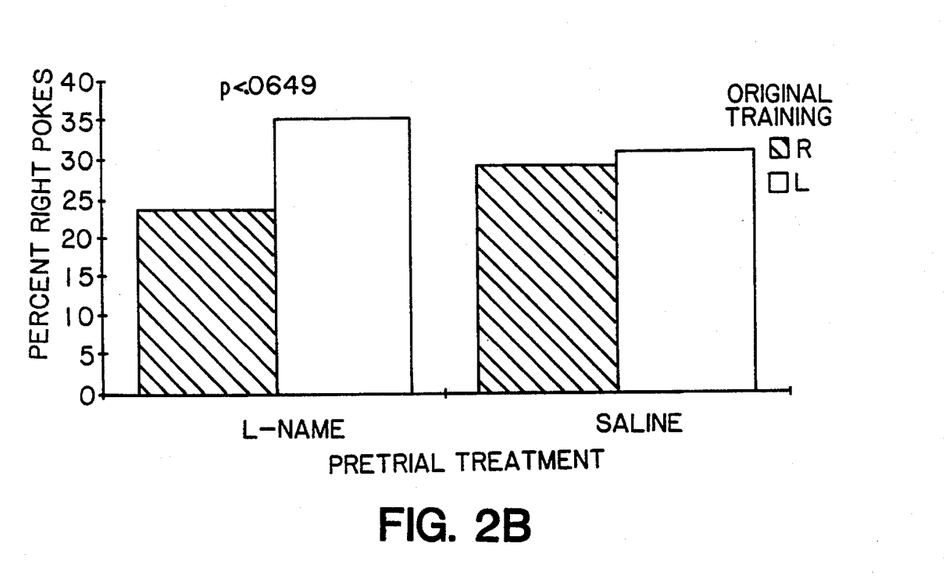
Figure 3A:
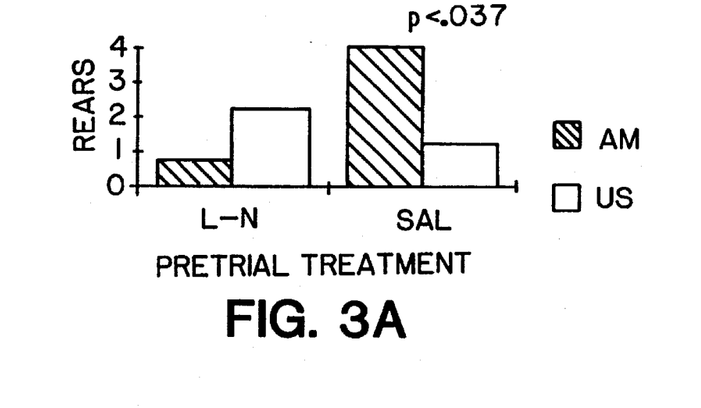
FIG. 3 shows the decreased rearing, locomotion and perseveration without loss of exploratory holepoking during extinction under $N^G$-nitro-L-arginine methyl ester in amphetamine treated animals. AM=prenatal d-amphetamine exposure; US=undernourished+saline injection controls; L-N=L-NAME; SAL=saline. p-values from t-tests, *=one-tailed.
Figure 3B:
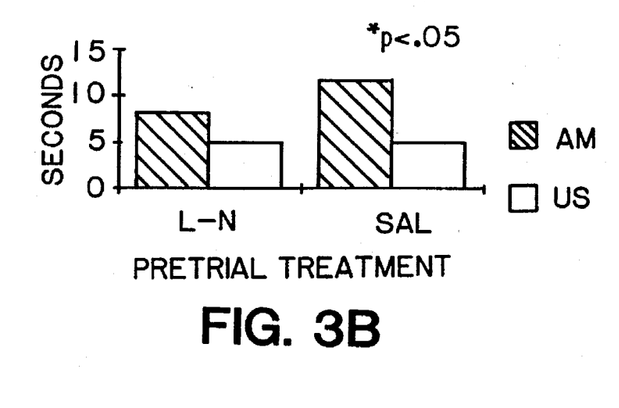
Figure 3C:
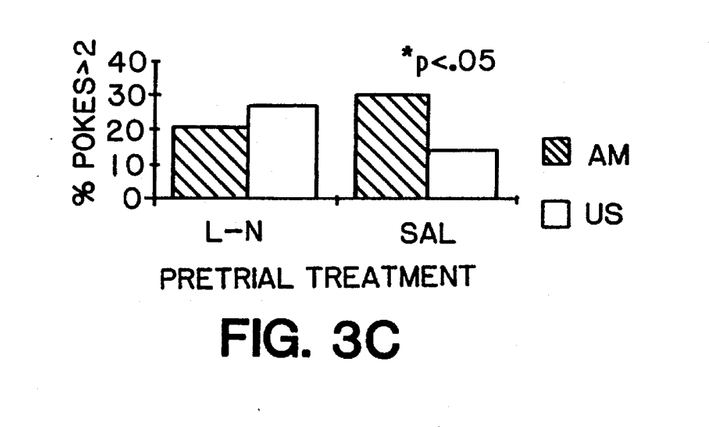
Figure 3D:
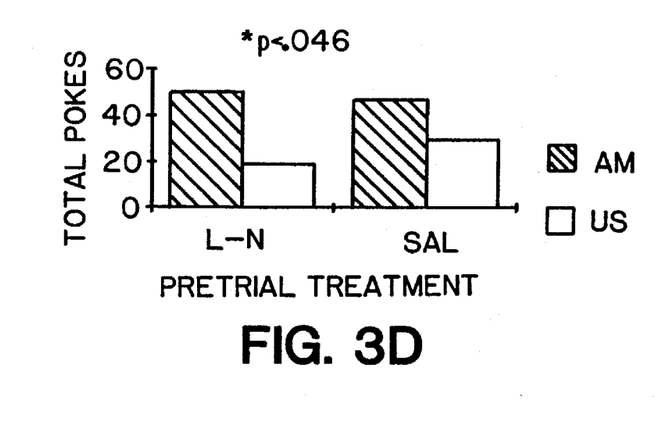

The main results following apomorphine treatment are shown in Table I. Under saline, amphetamine treated males showed significantly more walking activity than control animal and correspondingly lower HEAD↓ and STILL scores than undernourished control animals. Under apomorphine, amphetamine treated animals were so much more reduced in walking than control animals that the treatment groups no longer differed on this score, or in rearing (FIG. 1). Female amphetamine treated animals showed significantly more licking and gnawing under apomorphine than undernourished control animals. Because an increased dopamine effect will result in less walking and more licking, this indicated an increased sensitivity to dopaminergic challenge in the amphetamine treated animals, which is in agreement with the behavioral results from holeboard learning with these same animals. It was also apparent that the undernourished control animals differ from both the amphetamine treated and control groups in their response to apomorphine.

TABLE I

Litter-based t-test statistics for behavioral ratings of amphetamine treated, control, or undernourished offspring challenged with apomorphine

| VAR | DOSE | MEANS ± S.E. | | t | p | TREND |
| --- | --- | --- | --- | --- | --- | --- |
| WALK | 0.0 | 6.14 ± 0.7 | 4.17 ± 0.6 | 2.0 | *0.03 | AM > CO |
| HEAD↓ | 0.0 | 2.43 ± 0.2 | 5.33 ± 1.1 | 2.5 | *0.04 | AM < UN |
| HEAD↓ | 0.0 | 2.33 ± 0.5 | 5.33 ± 1.1 | 2.6 | 0.03 | CO < UN |
| STILL | 0.5 | 0.14 ± 0.1 | 1.13 ± 0.4 | 2.69 | 0.02 | AM < UN |
| LICK | 0.5 | 13.29 ± 1.3 | 6.75 ± 3.3 | 2.17 | *0.03 | AM < UN |
| HEAD↓ | 1.0 | 9.10 ± 2.78 | 0.67 ± 0.47 | 2.99 | 0.04 | CO > UN |

VAR = behavioral variable; t = t-test value; p = probability value.
*one-tailed test Physostigmine Challenge The results under physostigmine challenge are shown in Table II. The control animals were significantly less still and walked more than both the amphetamine and undernourished groups under the saline condition. With 0.1 mg/kg physostigmine, amphetamine treated animals, especially the females, now generated the greatest amount of walking. Under 0.6 mg/kg physostigmine these differences disappeared as walking was strongly reduced in all treatment groups.

The HEAD↓ response showed a similar trend. Under the saline test, both control and undernourished animals were significantly more in this position than the amphetamine treated group. However, under the influence of 0.1 mg/kg physostigmine, all treatment groups show decreased HEAD↓ activity, but the amphetamine treated animals had the greatest amount of HEAD↓ activity. At 0.6 mg/kg, there was virtually no activity directed at the floor for any treatment group. Rearing was significantly reduced in both amphetamine and undernourished groups, compared to control animals under the 0.1 mg/kg physostigmine treatment (see FIG. 1).

Teeth chattering or gnashing, which is a characteristic sign of cholinergic stimulation, was not present at all under saline, but began to appear in female amphetamine animals under the 0.1 mg/kg physostigmine challenge, and was significantly greater than in control animals at the 0.6 mg/kg dose level. Although not reaching the level of the amphetamine animals, undernourished control females had significantly more teeth chattering at the 0.6 mg/kg level than the corresponding CO control animals.

TABLE II

Litter-based t-test statistics for behavioral rating scores of amphetamine control and undernourished offspring challenged with physostigmine

| VAR | SEX | DOSE | MEANS ± S.E. | | t | p | TREND |
|---|---|---|---|---|---|---|---|
| STILL | m/f | 0.0 | 2.61 ± 0.4 | 5.75 ± 1.2 | 3.04 | 0.01 | AM < UN |
| WALK | f | 0.0 | 7.29 ± 0.4 | 9.70 ± 1.0 | 2.41 | 0.04 | AM < CO |
| WALK | m/f | 0.0 | 6.93 ± 0.1 | 4.75 ± 0.1 | 10.62 | 0.00 | AM > UN |
| WALK | f | 0.0 | 9.70 ± 1.0 | 4.92 ± 0.3 | 3.92 | 0.01 | CO > UN |
| HEAD↓ | f | 0.0 | 4.64 ± 0.7 | 7.30 ± 0.9 | 2.26 | 0.05 | AM < CO |
| HEAD↓ | m | 0.0 | 4.00 ± 0.9 | 6.75 ± 0.2 | 2.76 | 0.04 | CO > UN |
| STILL | m/f | 0.1 | 9.71 ± 0.9 | 14.33 ± 0.4 | 3.66 | 0.01 | AM < UN |
| STILL | m/f | 0.1 | 11.28 ± 1.2 | 14.33 ± 0.4 | 2.45 | 0.05 | CO < UN |
| REAR | m | 0.1 | 0.79 ± 0.3 | 2.33 ± 0.7 | 2.22 | 0.05 | AM < CO |
| REAR | m/f | 0.1 | 2.46 ± 0.6 | 0.67 ± 0.4 | 2.20 | 0.05 | AM > UN |
| REAR | m/f | 0.1 | 2.28 ± 0.6 | 0.67 ± 0.4 | 2.07 | 0.03 | CO > UN |
| WALK | m/f | 0.1 | 4.64 ± 0.6 | 2.08 ± 0.5 | 2.72 | 0.02 | AM > UN |
| HEAD | m/f | 0.1 | 2.32 ± 0.5 | 0.58 ± 0.4 | 2.47 | 0.04 | AM > UN |
| TEETH | f | 0.6 | 4.57 ± 0.9 | 1.80 ± 0.5 | 2.35 | 0.04 | AM > CO |
| TEETH | f | 0.6 | 1.80 ± 0.5 | 3.92 ± 0.6 | 2.70 | 0.03 | CO < UN |

All tests were two-tailed

To summarize the physostigmine effects, amphetamine treated animals were more sensitive than saline injected or undernourished controls to several effects of the acetylcholine challenge. Undernourished animals showed only one sign of greater sensitivity to cholinergic challenge, i.e., increased teeth chattering at the maximum dose level.

EXAMPLE 3

Nitroglycerin Challenge

Nitroglycerin was used because of the increased number of nitric oxide synthetase-containing cholinergic neurons in the brainstem. Nitric oxide has a relaxing effect on central and peripheral blood vasculature, and a non-adrenergic, non-cholinergic, smooth muscle relaxant effect on several internal organs. The only specific overt behavior demonstrated to depend on nitric oxide is penile erection. However, the release of nitric oxide from the larger number of cholinergic neurons in the PPTg might lead to some form of increased interaction with the dopamine and acetylcholine systems. Nitroglycerin was tested at dose levels of 3.0, 5.0, and 7.0 mg/kg. However, only the 5.0 mg/kg dose resulted in significant behavioral changes and this dose was therefore selected for comparison with the other drugs.

For these, 10 amphetamine treated animals, 8 saline control animals and 6 undernourished control pups, all males, were used as subjects. A counterbalanced series of tests with nitroglycerin was run with 3.0, 5.0, and 7.0 mg/kg given on alternate days for each animal, except for four amphetamine animals that were tested only at 5.0 mg/kg. Animals were injected almost simultaneously, with observations blind to treatment conditions, beginning 10 minutes postinjection and lasting for 10 minutes. The observer switched between animals every 15 seconds, yielding 20 observations per session.

The behavioral scoring scale was the same as in the apomorphine/physostigmine experiments, except that SNIFF was removed, as occurring too frequently to be useful in differentiating, and HEAD↓ was omitted as too difficult to score, since animals frequently were muscularly relaxed and close to the floor.

Nitroglycerin Results

Since stimulation of the excessive number of nitric oxide-containing cells in the brainstem of amphetamine rats increases dopamine activity in the striatum, the present invention shows that nitroglycerin causes an increase in dopamine-related activity. This was illustrated by the greater rearing, grooming and walking in male amphetamine animals given nitroglycerin, as compared to both control and undernourished controls. The differences were greatest between amphetamine and undernourished animals (TABLE III).

TABLE III

Behavioral changes associated with nitroglycerin challenge to amphetamine, control, and undernourished animals

| Behavior | Direction | Wilcoxon Test |
|---|---|---|
| STILL | AM < UN | p < 0.04 |
| REAR | AM > CO | p < 0.05* |
| REAR | AM > UN | p < 0.03 |
| WALK | AM > CO | p < 0.04* |
| GROOM | AM > CO | p < 0.05* |

Wilcoxon Rank Sum method.
*one-tailed test

It should be noted that rearing in amphetamine treated animals was significantly increased following nitroglycerin, but was decreased following the 0.1 mg/kg dose of physostigmine in the previous experiment. Furthermore, no significant differences in rearing occurred in male amphetamine treated animals following apomorphine (FIG. 1).

EXAMPLE 4

$N^G$-nitro-L-arginine methyl ester (L-NAME) Challenge $N^G$-nitro-L-arginine methyl ester, from Research Biochemicals, Inc., Natick, Mass., was used because of its strong inhibitory effect on the reduction of nitric oxide synthetase to nitric oxide and citrulline. $N^G$-nitro-L-arginine methyl ester can significantly reduce blood flow in the choroid plexus of the rat by 16% at a dose of only 0.1 mg/kg i.v. and at 50 mg/kg i.p. can cause up to 50% reduction in nitric oxide synthetase activity in the brain. These changes are relatively long-lasting so the $N^G$-nitro-L-arginine methyl ester was always given last on a given day, and at least two days were allowed between successive treatments when these were required.

No specific behavioral effects of $N^G$-nitro-L-arginine methyl ester were known at the time. $N^G$-nitro-L-arginine methyl ester was initially examined at dose levels of 20, 100, and 300 mg/kg, but no behavioral effect that differentiated experimental and control animals was found at the 20 mg/kg level and therefore only the higher doses were used.

Aged 60–90 day old Sprague-Dawley rats were used as subjects. Four different studies were performed:

Effects of $N^G$-Nitro-L-Arginine methyl ester

The main effect was a reduction in behavior, accompanied at the highest dose by muscular flaccidity and labored breathing. The 20 mg/kg dose produced no significant behavioral differences between the amphetamine and control animals. However, $N^G$-nitro-L-arginine methyl ester at 100 mg/kg, which should almost completely inhibit brain nitric oxide synthetase activity, caused male amphetamine treated animals to have greater STILL scores than male controls. This was significant (p<0.0041, t-test, two-tailed) at the 300 mg/kg dose level and at this dose, control animals also showed significantly more walking (p<0.0385, t-test, two-tailed) than amphetamine treated animals. Thus, the 100 and 300 mg/kg doses were used with d-amphetamine pretreatment and for comparison with the nitroglycerin data.

Comparison of Amphetamine vs. $N^G$-nitro-L-arginine methyl ester+Amphetamine:

Male sibling amphetamine treated (N=4) and sibling control animals (N=4) were divided into two groups consisting of 2 amphetamine and 2 control animals. One group was injected with 2.5 mg/kg d-amphetamine and 15 minutes later observed behaviorally. The second group was pretreated with an injection of 300 mg/kg L-NAME 24 hours before the 2.5 mg/kg d-amphetamine injection.

Although not statistically significant due to the small number of animals, both male amphetamine treated and control rats pretreated with $N^G$-nitro-L-arginine methyl ester 24 hours before d-amphetamine were consistently more still and had less walking than rats receiving only the d-amphetamine treatment.

Comparison of Nitroglycerin vs. L-NAME

Only male animals were used, amphetamine-treated as follows: 6 animals were injected s.c. with 5.0 mg/kg nitroglycerin, 4 animals were injected s.c. with $N^G$-nitro-L-arginine methyl ester at either 100 (N=2), or 300 (N=2), mg/kg. The control animals were divided similarly into: 6 animals treated with 5.0 mg/kg nitroglycerin and 4 animals treated with either 100 or 300 mg/kg $N^G$-nitro-L-arginine methyl ester. Because there were no significant differences between the 100 and 300 mg/kg $N^G$-nitro-L-arginine methyl ester treatment effects, these treatments were pooled for statistical analysis. Five minutes after injections, animals were observed behaviorally for 20 minutes.

For both amphetamine and control treatment conditions, the effects of 100 vs. 300 mg/kg L-NAME showed no differences and results from these dose levels were then pooled for the following comparisons.

The importance of nitric oxide is shown when the nitric oxide activity is greater following nitroglycerin than $N^G$-nitro-L-arginine methyl ester. Control animals under nitroglycerin vs. those under $N^G$-nitro-L-arginine methyl ester showed no significant behavioral differences, while the amphetamine animals under nitroglycerin showed significantly increased activity compared to those under $N^G$-nitro-L-arginine methyl ester treatment (Table IV).

TABLE IV

Behavioral effects of nitroglycerin and L-NAME in male amphetamine treated animals

| ACT | DIRECTION OF CHANGE | WILCOXON TEST |
|---|---|---|
| STILL | AM L-NAME > AM NITRO | p < 0.050 |
| REAR | AM NITRO > AM L-NAME | p < 0.060* n.s. |
| WALK | AM NITRO > AM L-NAME | p < 0.030* |
| GROOM | AM NITRO > AM L-NAME | p < 0.048* |

Wilcoxon Rank Sum method;
*one-tailed test; n.s. = not significant

Comparison: Amphetamine+Nitroglycerin vs. Amphetamine+L-NAME

Amphetamine treated animals (8 males; 2 females) and control animals (8 males; 2 females) were injected s.c. and observed behaviorally on three separate days with at least a two-day inter-trial interval. On Day 1 all animals received 2.5 mg/kg d-amphetamine followed 15 minutes later by behavioral observation. On Day 2, all animals received 2.5 mg/kg d-amphetamine followed 5 minutes later by 5.0 mg/kg nitroglycerin, with the observation period beginning 10 minutes after the final injection. On Day 3, all animals received 2.5 mg/kg d-amphetamine followed 5 minutes later by 300 mg/kg $N^G$-nitro-L-arginine methyl ester, with the observation period beginning 10 minutes after the final injection. Observational methods for all $N^G$-nitro-L-arginine methyl ester studies were the same as before except for the addition of "head-up" or "head-horizontal" positions, and a 0=NONE, 1=SOME, 2=CONTINUOUS ranking score for the activity measures.

Amphetamine treated males showed significantly more walking under d-amphetamine alone than they did under either the (amphetamine+nitroglycerin) or (amphetamine+L-NAME) condition (p=0.003; F=7.60; df=21).

Under combined treatment with 2.5 mg/kg d-amphetamine+300 mg/kg $N^G$-nitro-L-arginine methyl ester, very little activity was observed and most amphetamine and control animals sat still and had labored breathing. However, amphetamine animals had less walking and a significantly greater HEAD↓ score (p=0.042, Wilcoxon, two-tailed) than the control animals.

Thus, the nitroglycerin treatment produced more activity in amphetamine treated animals than did $N^G$-nitro-L-arginine methyl ester, and neither of these differences existed in control animals. Although the increase in rearing in AM-NITRO animals did not quite reach the p=0.05 significance level, it demonstrated a trend in line with the previous effects of nitroglycerin.

EXAMPLE 5

Summary of the Similarities and Differences Between the Dopamine, Acetylcholine and Nitric Oxide Challenge Effects TABLE V shows a summary of the basic similarities and differences between the dopamine, acetylcholine and nitric oxide challenge effects on unconditioned behaviors. Together with the data on conditioned (learned) behavior discussed above, these data demonstrate that the animal model produces abnormal behaviors that are similar to those seen in schizophrenia and related illnesses with a hyperdopaminergic component. Furthermore, the present invention shows that these abnormal behaviors of both conditioned and unconditioned types, can be altered in a beneficial manner by treatment with a nitric oxide synthetase inhibitor.

TABLE V

Behavioral findings with AM animals under dopaminergic (apomorphine) or cholinergic (physostigmine) stimulation at low or high dose levels, compared with nitric oxide releasing or inhibiting (nitroglycerin vs. L-NAME) treatment

| ACT | DESCRIPTION | APOM DA↑ | APOM DA↑↑ | PHYSO ACh↑ | PHYSO ACh↑↑ | NITRO NO↑ | L-N NO↓ |
|---|---|---|---|---|---|---|---|
| STILL | No body movement. | ↓ | ↑ | ↓ | ↑ | ↓ | ↑↑ |
| LICK | Licking cage or floor. | 0 | ↑↑ | 0 | 0 | 0 | 0 |
| GNAW | Mouthing/biting objects | 0 | ↑↑ | 0 | 0 | 0 | 0 |
| TEETH | Chatter/gnashing teeth | 0 | 0 | 0 | ↑ | 0 | 0 |
| REAR | Rearing on hindlegs | ↑ | 0 | ↑ | = | ↑ | 0 |
| WALK | Locomotion, four limbs. | ↑ | 0 | ↑ | ↓ | ↑ | ↓↓ |
| GROOM | Grooming head/body. | ↑ | 0 | = | 0 | ↑ | 0 |
| HEAD↑* | Head mainly up. | {= | 0 | ↑ | ↑} | = | ↑ |
| HEAD↔* | Horizontal, or up/down | {= | = | = | ↑↑} | ↑ | ↑↑ |
| HEAD↓ | Head mainly down. | 0 | ↑↑ | 0 | = | 0 | = |

↑↑ or ↑ - increased frequency; ↓↓ or ↓ - decreased frequency; = - not different from non-drug state; 0 - not present or very rare.
*these scores tested here only in nitroglycerin and L-NAME experiments.
{ } = findings from other experiments for comparison Any patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating a brain disease characterized by excess activity of a brain dopaminergic system, comprising the step of administering an inhibitor of brain nitric oxide synthetase to an individual having said disease.

2. The method of claim 1, wherein said inhibitor of brain nitric oxide synthetase is selected from the group consisting of nitro-L-arginine, N-imino ethyl-L-ornithine, L-canavanine and N-monomethyl-L-arginine.

3. The method of claim 1, wherein said inhibitor of brain nitric oxide synthetase is nitro-L-arginine or a methyl ester thereof.

4. The method of claim 3, wherein said nitro-L-arginine is administered in an amount of from about 1 milligrams/kg to about 30 milligrams/kg.

5. The method of claim 1, wherein said brain disease is selected from the group consisting of schizophrenia, Tourette's Syndrome, mania, autism and obsessive compulsive disorder.

6. A method of pharmacologically treating schizophrenia, comprising the step of administering an inhibitor of brain nitric oxide synthetase to an individual in need of treatment.

7. The method of claim 6, wherein said inhibitor of brain nitric oxide synthetase is selected from the group consisting of nitro-L-arginine, N-imino ethyl-L-ornithine, L-canavanine and N-monomethyl-L-arginine.

8. The method of claim 6, wherein said inhibitor of brain nitric oxide synthetase is nitro-L-arginine or a methyl ester thereof.

9. The method of claim 6, wherein said nitro-L-arginine is present in an amount of from about 5 milligrams/kg to about 30 milligrams/kg.

* * * * *